US00PP36174P2

(12) United States Plant Patent
Nir

(10) Patent No.: US PP36,174 P2
(45) Date of Patent: Oct. 1, 2024

(54) ***CHAMELAUCIUM* PLANT NAMED 'MOON'**

(50) Latin Name: *Chamelaucium uncinatum*
Varietal Denomination: MOON

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 17 days.

(21) Appl. No.: 18/214,046

(22) Filed: Jun. 26, 2023

(30) Foreign Application Priority Data

Feb. 7, 2023 (EM) ..... 2023/0334

(51) Int. Cl.
*A01H 5/00* (2018.01)
*A01H 6/00* (2018.01)

(52) U.S. Cl.
USPC ..... Plt./229

(58) Field of Classification Search
USPC ..... Plt./226, 229
See application file for complete search history.

(56) References Cited

U.S. PATENT DOCUMENTS

PP28,274 P2 * 8/2017 Nir ..... A01H 6/00
Plt./229

* cited by examiner

*Primary Examiner* — Karen M Redden
(74) *Attorney, Agent, or Firm* — Cassandra Bright

(57) ABSTRACT

A new and distinct cultivar of *Chamelaucium* plant named 'MOON' is disclosed, characterized by abundant, small white flowers. Flower production begins in winter. The new cultivar is a *Chamelaucium*, normally producing cut flower stems, or as a garden or container plant.

1 Drawing Sheet

Latin name of the genus and species: *Chamelaucium uncinatum.*

Variety denomination: 'MOON'.

BACKGROUND OF THE INVENTION

The new *Chamelaucium* cultivar is the product of a planned breeding program conducted by the inventor, Nitzan Nir, in Kfar Hess, Israel. The objective of the breeding program was to produce new *Chamelaucium* varieties for ornamental commercial applications. The crossing resulting in this new cultivar was made in March 2016 at a commercial nursery in Kfar Hess, Israel.

The seed parent is the unpatented proprietary cultivar referred to as *Chamelaucium uncinatum* 'C-14.32'. The pollen parent is the unpatented proprietary cultivar referred to as *Chamelaucium uncinatum* 'Atar E'. The new cultivar was discovered in February 2019 by the inventor in a group of seedlings resulting from previously mentioned crossing, in a commercial nursery in Kfar Hess, Israel.

Asexual reproduction of the new cultivar has been performed by terminal vegetative cuttings. This was first performed in April 2019 at a commercial nursery in Kfar Hess, Israel in and has shown that the unique features of this cultivar are stable and reproduced true to type in at least 6 successive generations.

SUMMARY OF THE INVENTION

The cultivar 'MOON' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MOON'. These characteristics in combination distinguish 'MOON' as a new and distinct *Chamelaucium* cultivar:

1. Winter blooming.
2. Small flower size.
3. White flower color.
4. Small bud size.
5. Terminal flowering.

PARENT COMPARISON

Plants of the new cultivar 'MOON' are similar to plants of the seed parent in most horticultural characteristics, however, plants of the new cultivar 'MOON' differ in the following:

1. The new cultivar blooms in winter, while the seed parent blooms in spring.
2. Flower color of the new cultivar is white, while the flower color of the seed parent is pinkish-white.

Plants of the new cultivar 'MOON' are similar to plants of the pollen parent in most horticultural characteristics, however, plants of the new cultivar 'MOON' differ in the following:

1. Buds of the new cultivar are smaller by about 30 to 50 percent than buds of the pollen parent.
2. Flowers of the new cultivar are smaller by about 30 to 50 percent than flowers of the pollen parent.
3. The new cultivar flowers terminally, while the pollen parent flowers continuously along the stem.

COMMERCIAL COMPARISON

Plants of the new cultivar 'MOON' are comparable to the cultivar *Chamelaucium uncinatum* 'Solar', U.S. Plant Pat.

No. 32,084. The two *Chamelaucium* cultivars are similar in most horticultural characteristics; however, the new cultivar 'MOON' differs in the following:

1. Flower color of the new cultivar is white, while the flower color of this comparator is pink.
2. The new cultivar blooms in winter, while this comparator blooms in autumn.

Plants of the new cultivar 'MOON' are comparable to the cultivar *Chamelaucium uncinatum* 'Jupiter', U.S. Plant Pat. No. 27,255. The two *Chamelaucium* cultivars are similar in most horticultural characteristics; however, the new cultivar 'MOON' differs in the following:

1. The new cultivar blooms in winter, while this comparator blooms in autumn.
2. Flower color of the new cultivar is white, while the flower color of this comparator is purple.

BRIEF DESCRIPTION OF THE PHOTOGRAPH

The accompanying photograph in FIG. 1 illustrates in full color typical mature flowering stems of 'MOON' harvested from a plant of the new cultivar at approximately 1 to 2 years of age.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'MOON' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types.

Botanical classification: *Chamelaucium uncinatum* 'MOON'.

Age of plant described: About 2 months old from a rooted cutting.

Typical flowering stems harvested per plant: 80 to 100.

Vase life of flowers: Two weeks.

PROPAGATION

Time to produce a rooted plantlet: 30 to 60 days at approximately 24° C.

Root description: Split root.

PLANT

Growth habit: Upright.

Height: 150 cm to top of flowers.

Plant spread: 80 cm.

Branching characteristics:

Length of primary lateral branches: 60 cm and up on average.

Diameter of lateral branches: 0.08 to 0.26 cm (branches from the top 30 cm of the primary lateral branch).

Quantity of primary lateral branches: 80 to 100.

Characteristics of primary lateral branches:

*Diameter.*—0.5 to 0.7 cm, measured at 50 cm from top.

*Color.*—Near RHS Brown 200C.

*Texture.*—Smooth.

*Strength.*—Low flexibility.

Internode length: Range from 2 to 6 cm, section of top 30 cm.

FOLIAGE

Leaf:

*Arrangement.*—Opposite.

*Quantity.*—Approximately 8 leaves, in the 10-15 cm section from the top of the branch.

*Average length.*—1.7 cm.

*Average width.*—0.9 mm.

*Shape of blade.*—Needle.

*Apex.*—Acute.

*Base.*—Truncate.

*Margin.*—Entire.

*Texture.*—Smooth.

*Pubescence.*—None.

*Aspect.*—Straight.

*Color.*—Young foliage, upper side: Near RHS Green 137C. Young foliage, under side: Near RHS Green 137C. Mature foliage, upper side: Near RHS Green 137A. Mature foliage, under side: Near RHS Green 137A.

*Venation.*—Indistinguishable from foliage.

*Petiole.*—Not present.

FLOWER

Natural flowering season: Winter.

Days to flowering from rooted cutting: Photoperiodic conditions. No juvenility.

Individual flower type: 5 petals, about 1.6 cm in diameter.

Rate of flower opening: About 45 to 60 days from bud to fully opened flower.

Persistent or self-cleaning: Self-cleaning.

Bud:

*Shape.*—Round.

*Length.*—0.5 cm.

*Diameter.*—0.45 cm.

*Color.*—Near RHS White 155C.

Flower size:

*Diameter.*—1.6 cm.

*Length.*—0.9 cm.

Corolla:

*Petals.*—Arrangement: Rotate hypanthium. Length: 0.5 cm. Diameter: 0.65 cm. Quantity: 5. Texture: Smooth. Apex: Round. Base: Fused.

*Color.*—When opening: Upper surface: Near RHS White 155C. Lower surface: Near RHS White 155C. Fully opened: Upper surface: Near RHS White 155C. Lower surface: Near RHS White 155C. Aging: Upper surface: Near RHS White 155C. Lower surface: Near RHS White 155C.

Interior corolla/tube:

*Diameter.*—0.65 cm.

*Length.*—0.3 cm.

*Color.*—When opening: Upper surface: Near RHS Yellow-Green 144A. Lower surface: Near RHS Yellow 160B. Fully opened: Upper surface: Near RHS Yellow-Green 144A. Lower surface: Near RHS Yellow 160B. Aging: Upper surface: Near RHS Yellow-Green 146C. Lower surface: Near RHS Yellow-Green 146C.

Calyx/sepals:

*Quantity per flower.*—5.

*Shape.*—Oval.

*Length.*—0.24 cm.

*Width.*—0.3 cm.

*Margin.*—Smooth.

*Texture.*—Smooth.

*Color.*—Near RHS Yellow-Green 146C.

Peduncle: Peduncle consists of the plant stem.

Pedicel:

*Length.*—0.5 to 0.9 cm.

*Diameter.*—0.7 to 0.1 cm.

*Color.*—Near RHS Yellow-Green 144A.

Fragrance: None.

REPRODUCTIVE ORGANS

Stamens:

*Number.*—10.

*Filament length.*—2 mm.

*Filament color.*—RHS White 155C.

Anthers:

*Shape.*—Oval.

*Length.*—0.5 mm.

*Color.*—Near RHS Yellow 2C.

Pollen: Not observed.

Pistil:

*Number.*—1.

*Length.*—0.55 to 0.6 cm.

*Style Length.*—0.5 to 0.55 cm.

*Style color.*—Near RHS White 157B.

*Stigma.*—Shape: Round. Color: Near RHS Yellow-Green 152D.

OTHER CHARACTERISTICS

Seeds and fruits: Single flower produces one fruit. When the fruit is fertile, it will produce 1 seed. Fruit and seeds are too small for accurate measurement of characteristics.

Disease/pest resistance: Neither resistance nor susceptibility to the normal diseases and pests of *Chamelaucium* have been observed to date.

Temperature tolerance: From −2° C. to 35° C.

What is claimed is:

1. A new and distinct cultivar of *Chamelaucium* plant named 'MOON' as herein illustrated and described.

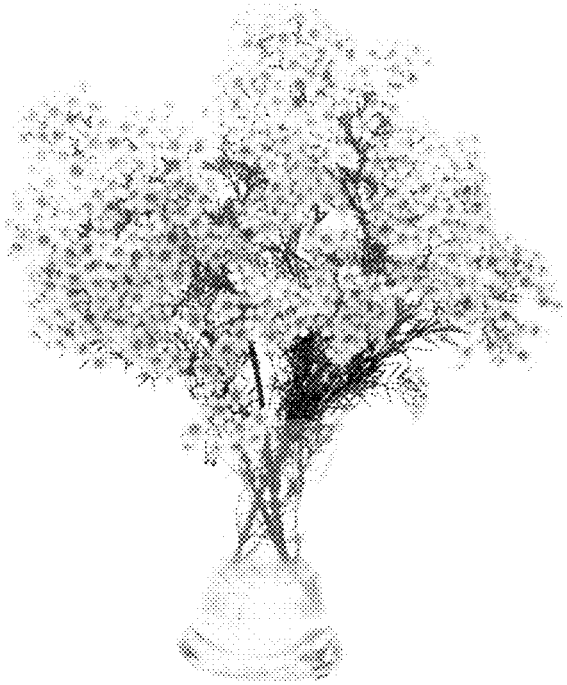

* * * * *